(12) United States Patent
Schelberger et al.

(10) Patent No.: US 6,245,798 B1
(45) Date of Patent: Jun. 12, 2001

(54) FUNGICIDAL MIXTURES

(75) Inventors: Klaus Schelberger, Gönnheim; Reinhold Saur, Böhl-Iggelheim; Hubert Sauter, Mannheim; Bernd Müller, Frankenthal; Erich Birner, Altleiningen; Joachim Leyendecker, Ladenburg; Eberhard Ammermann, Heppenheim; Gisela Lorenz, Neustadt; Siegfried Strathmann, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/423,963

(22) PCT Filed: May 18, 1998

(86) PCT No.: PCT/EP98/02911

§ 371 Date: Nov. 17, 1999

§ 102(e) Date: Nov. 17, 1999

(87) PCT Pub. No.: WO98/53692

PCT Pub. Date: Dec. 3, 1998

(30) Foreign Application Priority Data

May 30, 1997 (DE) ................................. 197 22 657

(51) Int. Cl.⁷ .......................... A01N 43/56; A01N 37/18; A01N 43/64
(52) U.S. Cl. ...................... 514/407; 514/383; 514/619
(58) Field of Search ................... 514/383, 407, 514/619

(56) References Cited

U.S. PATENT DOCUMENTS 5,504,110  4/1996  Wingert et al. ............... 514/539

FOREIGN PATENT DOCUMENTS

| 93/15046 | 8/1993 | (WO) . |
| 95/18789 | 7/1995 | (WO) . |
| 96/01256 | 1/1996 | (WO) . |
| 96/01258 | 1/1996 | (WO) . |
| 96/03047 | 2/1996 | (WO) . |
| 97/06679 | 2/1997 | (WO) . |

*Primary Examiner*—Allen J. Robinson
(74) *Attorney, Agent, or Firm*—Keil & Weinkauf

(57) ABSTRACT

A fungicidal mixture, comprising
a) a carbamate of the formula I,

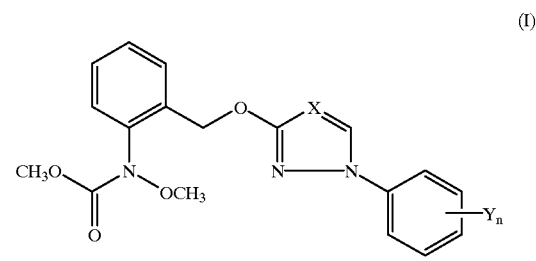

in which X is CH or N, n is 0, 1 or 2 and Y is halogen, $C_1$–$C_4$-alkyl or $C_1$–$C_4$-haloalkyl, it being possible for the radicals Y to be different if n is 2, or a salt or adduct thereof, and b) an oxime ether carboxamide of the formula II

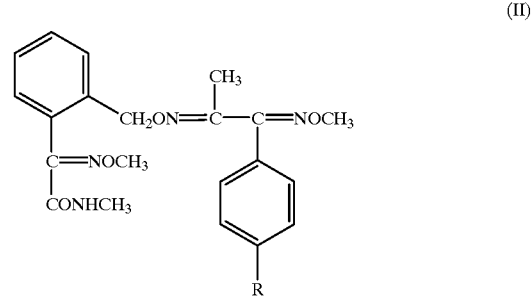

in which R represents hydrogen or halogen in a synergistically effective amount.

14 Claims, No Drawings

FUNGICIDAL MIXTURES

This application is a 371 of PCT/EP98/02911, filed May 18, 1998.

The present invention relates to a fungicidal mixture which comprises a) a carbamate of the formula I,

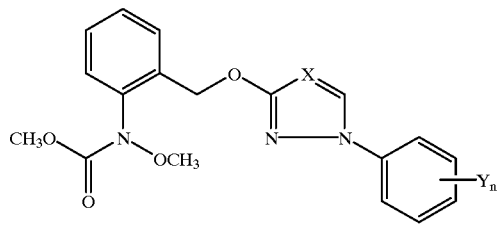

in which X is CH or N, n is 0, 1 or 2 and Y is halogen, $C_1$–$C_4$-alkyl or $C_1$–$C_4$-haloalkyl, it being possible for the radicals Y to be different if n is 2, or a salt or adduct thereof, and b) an oxime ether carboxamide of the formula II

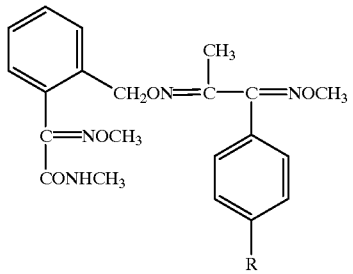

in which R represents hydrogen or halogen in a synergistically effective amount.

Moreover, the invention relates to methods for controlling harmful fungi using mixtures of the compounds I and II and to the use of the compounds I and the compounds II for preparing such mixtures.

The compounds of the formula I, their preparation and their activity against harmful fungi are disclosed in the literature (WO-A 93/15,046; WO-A 96/01,256 and WO-A 96/01,258).

Also disclosed are the compounds of the formula II, their preparation and their activity against harmful fungi (WO-A 95/18,789).

It is an object of the present invention to provide mixtures which have improved activity against harmful fungi combined with a reduced total amount of active ingredients applied (synergistic mixtures), with a view to reducing the application rates and to improving the activity spectrum of the known compounds I and II.

We have found that this object is achieved by the mixture defined at the outset. Moreover, we have found that better control of harmful fungi is possible by applying the compounds I and the compounds II simultaneously, that is either together or separately, or by applying the compounds I and the compounds II in succession than when the individual compounds are used.

The formula I in particular represents carbamates in which the combination of the substituents corresponds to a row of the following table:

(I)

| No. | X | $Y_n$ |
|---|---|---|
| I.1 | N | 2-F |
| I.2 | N | 3-F |
| I.3 | N | 4-F |
| I.4 | N | 2-Cl |
| I.5 | N | 3-Cl |
| I.6 | N | 4-Cl |
| I.7 | N | 2-Br |
| I.8 | N | 3-Br |
| I.9 | N | 4-Br |
| I.10 | N | 2-$CH_3$ |
| I.11 | N | 3-$CH_3$ |
| I.12 | N | 4-$CH_3$ |
| I.13 | N | 2-$CH_2CH_3$ |
| I.14 | N | 3-$CH_2CH_3$ |
| I.15 | N | 4-$CH_2CH_3$ |
| I.16 | N | 2-$CH(CH_3)_2$ |
| I.17 | N | 3-$CH(CH_3)_2$ |
| I.18 | N | 4-$CH(CH_3)_2$ |
| I.19 | N | 2-$CF_3$ |
| I.20 | N | 3-$CF_3$ |
| I.21 | N | 4-$CF_3$ |
| I.22 | N | 2,4-$F_2$ |
| I.23 | N | 2,4-$Cl_2$ |
| I.24 | N | 3,4-$Cl_2$ |
| I.25 | N | 2-Cl, 4-$CH_3$ |
| I.26 | N | 3-Cl, 4-$CH_3$ |
| I.27 | CH | 2-F |
| I.28 | CH | 3-F |
| I.29 | CH | 4-F |
| I.30 | CH | 2-Cl |
| I.31 | CH | 3-Cl |
| I.32 | CH | 4-Cl |
| I.33 | CH | 2-Br |
| I.34 | CH | 3-Br |
| I.35 | CH | 4-Br |
| I.36 | CH | 2-$CH_3$ |
| I.37 | CH | 3-$CH_3$ |
| I.38 | CH | 4-$CH_3$ |
| I.39 | CH | 2-$CH_2CH_3$ |
| I.40 | CH | 3-$CH_2CH_3$ |
| I.41 | CH | 4-$CH_2CH_3$ |
| I.42 | CH | 2-$CH(CH_3)_2$ |
| I.43 | CH | 3-$CH(CH_3)_2$ |
| I.44 | CH | 4-$CH(CH_3)_2$ |
| I.45 | CH | 2-$CF_3$ |
| I.46 | CH | 3-$CF_3$ |
| I.47 | CH | 4-$CF_3$ |
| I.48 | CH | 2,4-$F_2$ |
| I.49 | CH | 2,4-$Cl_2$ |
| I.50 | CH | 3,4-$Cl_2$ |
| I.51 | CH | 2-Cl, 4-$CH_3$ |
| I.52 | CH | 3-Cl, 4-$CH_3$ |

Particular preference is given to the compounds I.12, I.23, I.32 and I.38.

In the formula II, R is hydrogen or a halogen atom such as fluorine, chlorine, bromine and iodine, especially hydrogen, fluorine and chlorine, in particular hydrogen or fluorine.

In relation to the C=N double bonds, the compounds of the formula II can be present in the E or the Z configuration (in relation to the carboxylic acid function). Accordingly, they can be used in the mixture according to the invention in each case either in the form of a pure E or Z isomer or else in the form of an E/Z isomer mixture. The E/Z isomer mixture or the E isomer is preferably used, the E isomer being especially preferred.

The C=N double bonds of the oxime ether groups in the side chain of the compounds II can exist in each case in the form of pure E or Z isomers or in the form of E/Z isomer mixtures. The compounds II can be used in the mixtures according to the invention as isomer mixtures or else as the pure isomers. With a view to their use, compounds II which are particularly preferred are those where both oxime ether groups in the side chain are in the E configuration (E/E).

Owing to the basic character of their nitrogen atoms, the compounds I and II are capable of forming salts or adducts with inorganic or organic acids or with metal ions.

Examples of inorganic acids are hydrohalic acids such as hydrofluoric acid, hydrochloric acid, hydrobromic acid and hydriodic acid, and furthermore, sulfuric acid, phosphoric acid and nitric acid.

Suitable organic acids are, for example, formic acid, carboxylic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or aryl disulfonic acids (aromatic radicals, such as phenyl and naphtbyl which carry one or two sulfo groups), alkylphosphonic acids (phosphonic acids having straight-chain or branched alkyl radicals of 1 to 20 carbon atoms), arylphosphonic acids or aryl diphosphonic acids (aromatic radicals such as phenyl and naphthyl, which carry one or two phosphonic acid radicals), it being possible for the alkyl or aryl radicals to carry further substituents, for example p-toluenesulfonic acid, salicylic acid, p-amino salicylic acid, 2-phenoxybenzoic acid, 2-acetoxybenzoic acid, etc.

Suitable metal ions are, in particular, the ions of the elements of the first to eighth sub-groups, in particular chromium, manganese, iron, cobalt, nickel, copper, zinc, and furthermore of the second main group, in particular calcium and magnesium, and of the third and fourth main groups, in particular aluminum, tin and lead. The metals can exist in the various valencies which they can assume.

When preparing the mixtures, it is preferred to employ the pure active ingredients I and II, to which further active ingredients against harmful fungi or other pests, such as insects, arachnids or nematodes, or else herbicidal or growth-regulating active ingredients or fertilizers can be admixed, if so required.

The mixtures of the compounds I and II, or the simultaneous joint and separate use of the compounds I and II, exhibit outstanding activity against a wide range of phytopathogenic fungi, in particular from the classes of the ascomycetes, basidiomycetes, phycomycetes and deuteromycetes. Some of them act systemically and can therefore be employed as foliar and soil-acting fungicides.

They are especially important for controlling a large number of fungi in a variety of crop plants, such as cotton, vegetable species (e.g. cucumbers, beans, tomatoes, potatoes and cucurbits) barley, grass, oats, bananas, coffee, maize, fruit species, rice, rye, soya, grapevine, wheat, ornamentals, sugarcane and a variety of seeds.

They are particularly suitable for controlling the following phytopathogenic fungi: *Erysiphe graminis* (powdery mildew) in cereals, *Erysiphe cichoracearum* and *Sphaerotheca fuliginea* in. cucurbits), *Podosphaera leucotricha* in apples, *Uncinula necator* in grapevines, Puccinia species in cereals, Rhizoctonia species in cotton, rice and lawns, Ustilago species in cereals and sugarcane, *Venturia inaequalis* (scab) in apples, Helminthosporium species in cereals, *Septoria nodorum* in wheat, *Botrytis cinerea* (gray mold) in strawberries, vegetables, ornamentals and grapevines, *Cercospora arachidicola* in groundnuts, *Pseudocercosporella herpotrichoides* in wheat and barley, *Pyricularia oryzae* in rice, *Phytophthora infestans* in potatoes and tomatoes, *Plasmopara viticola* in grapevines, Pseudoperonospora species in hops and cucumbers, Alternaria species in vegetables and fruit, Mycosphaerella species in bananas and Fusarium and Verticillium species.

Furthermore, they can be used in the protection of materials (e.g. in the protection of wood), for example against *Paecilomyces variotii*.

The compounds I and II can be applied simultaneously, either together or separately, or in succession, the sequence, in the case of separate application, generally not having any effect on the result of the control measures.

The compounds I and II are usually used in a weight ratio of 10:1 to 0.1:1, preferably 5:1 to 0.2:1, in particular 3:1 to 0.3:1.

Depending on the kind of effect desired, the application rates of the mixtures according to the invention are, in particular in agricultural crops, from 0.01 to 8 kg/ha, preferably 0.1 to 5 kg/ha, in particular 0.1 to 3.0 kg/ha.

The application rates of the compounds I are from 0.01 to 1 kg/ha, preferably 0.05 to 0.5 kg/ha, in particular 0.05 to 0.3 kg/ha.

Correspondingly, in the case of the compounds II, the application rates are from 0.01 to 1 kg/ha, preferably 0.02 to 0.5 kg/ha, in particular 0.05 to 0.3 kg/ha.

For seed treatment, the application rates of the mixture are generally from 0.001 to 250 g/kg of seed, preferably 0.01 to 100 g/kg, in particular 0.01 to 50 g/kg.

If phytopathogenic harmful fungi are to be controlled, the separate or joint application of the compounds I and II or of the mixtures of the compounds I and II is effected by spraying or dusting the seeds, the plants or the soils before or after sowing of the plants, or before or after plant emergence.

The fungicidal synergistic mixtures according to the invention, or the compounds I and II, can be formulated, for example in the form of ready-to-spray solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should guarantee as fine and uniform a distribution as possible of the mixture according to the invention.

The formulations are prepared in a manner known per se, e.g. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl, ethers alcohol polyglycol ether acetate, sorbitol esters, lignosulfite waste liquors or methylcellulose.

Powders, materials for broadcasting and dusts can be prepared by mixing or jointly grinding the compounds I or II or the mixture of the compounds I and II with a solid carrier.

Granules (e.g. coated granules, impregnated granules or homogeneous granules) are usually prepared by binding the active ingredient, or active ingredients, to a solid carrier.

Fillers or solid carriers are, for example, mineral earths, such as silicic acids, silica gels, silicates, talc, kaolin, limestone, lime, chalk, bole, loess, clay, dolomite, diatomaceous earth, calcium sulfate, magnesium sulfate, magnesium oxide, ground synthetic materials, and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise from 0.1 to 95% by weight, preferably 0.5 to 90% by weight, of one of the compounds I or II or of the mixture of the compounds I and II. The active ingredients are employed in a purity from 90% to 100%, preferably 95% to 100% (according to NMR spectrum or HPLC).

The compounds I or II, or the mixtures, or the corresponding formulations, are applied by treating the harmful fungi, their habitat, or the plants, seeds, soils, areas, materials or spaces to be kept free from them with a fungicidally effective amount of the mixture, or of the compounds I and II in the case of separate application.

The application can be effective before or after infection by the harmful fungi.

The synergistic activity of the mixtures according to the invention was demonstrated by the following experiments:

USE EXAMPLE 1

Curative activity against *Puccinia recondita* on wheat (wheat leaf rust)

Leaves of potted wheat seedlings of the variety "Frühgold" were dusted with spores of leaf rust (*Puccinia recondita*). Thereafter, the pots were kept for 24 hours in a chamber of high atmospheric humidity (90 to 95%) and 20 to 22° C. During this time, the spores germinated and the germinal tubes penetrated into the leaf tissue. The next day, the infected plants were sprayed to run off point with an aqueous formulation of active ingredient prepared from a stock solution consisting of 10% of active ingredient, 63% of cyclohexanone and 27% of emulsifier. After the spray coating had dried on, the test plants were kept for 7 days in a greenhouse at from 20 to 22° C. and 65 to 70% of relative atmospheric humidity. Thereafter, the extent of rust fungus development on the leaves was determined.

Evaluation was carried out by determining the infected leaf areas in percent. These percentages were converted into efficacy. The efficacy (E) was calculated as follows, using Abbot's formula:

$$E=(1-\alpha)\cdot 100/\beta$$

α corresponds to the fungal infection of the treated plants in % and

β corresponds to the fungal infection of the untreated (control) plants in %

An efficacy of 0 means that the infection level of the treated plants corresponds to that of the untreated control plants; an efficacy of 100 means that the treated plants were not infected.

The expected efficacies of the active ingredient mixtures were determined using Colby's formula [R. S. Colby, Weeds 15, 20–22 (1967)] and compared with the observed efficacies.

Colby's formula: $E=x+y-x\cdot y/100$

E expected efficacy, expressed in % of the untreated control, when using the mixture of the active ingredients A and B at the concentrations a and b x efficacy, expressed in % of the untreated control, when using active ingredient A at a concentration of a y efficacy, expressed in % of the untreated control, when using active ingredient B at a concentration of b The test results are shown in Tables 2 and 3.

TABLE 2

| Ex. | Active ingredient | Concentration of active ingredient in the spray liquor in ppm | Efficacy in % of the untreated control |
|---|---|---|---|
| 1C | Control (untreated) | (100% infection) | 0 |
| 2C | Compound I.32 from Tab. 1 = Ia.1 | 4<br>1 | 20<br>0 |
| 3C | Compound I.38 from Tab. 1 = Ia.2 | 4<br>1 | 0<br>0 |
| 4C | Comp. II.1 (R = H) | 4<br>1 | 0<br>0 |
| 5C | Comp. II.2 (R = F) | 1 | 0 |

TABLE 3

| Ex. | Mixture according to the invention | Observed efficacy | Calculated efficacy* |
|---|---|---|---|
| 6 | 4 ppa Ia.1 + 4 ppm II.1 | 100 | 20 |
| 7 | 4 ppm Ia.1 + 1 ppm II.1 | 95 | 20 |
| 8 | 1 ppm Ia.1 + 4 ppm II.1 | 50 | 0 |
| 9 | 1 ppm Ia.1 + 1 ppm II.2 | 30 | 0 |
| 10 | 4 ppm Ia.1 + 1 ppm II.2 | 99 | 20 |
| 11 | 4 ppm Ia.2 + 4 ppm II.1 | 90 | 0 |
| 12 | 4 ppm Ia.2 + 1 ppm II.1 | 90 | 0 |
| 13 | 1 ppm Ia.2 + 4 ppm II.1 | 40 | 0 |
| 14 | 4 ppm Ia.2 + 1 ppm II.2 | 80 | 0 |

*)calculated using Colby's formula

The test results show that the observed efficacy in all mixing ratios is higher than the efficacy which had been calculated beforehand using Colby's formula.

USE EXAMPLE 2

Activity against powdery mildew of wheat

Leaves of potted wheat seedlings of the variety "Frühgold" were sprayed to run off point with an aqueous formulation of active ingredient prepared from a stock solution consisting of 10% of active ingredient, 63% cyclohexanone and 27% of emulsifier. 24 hours after the spray coating had dried on, the leaves were dusted with spores of powdery mildew of wheat (*Erysiphe graminis* forma specialis tritici). The test plants were subsequently kept in a greenhouse at 20–24° C. and 60–90% relative atmospheric humidity. After 7 days, the extent of the mildew development was determined visually in % infection of the total leaf area.

The results are shown in Tables 4 and 5.

TABLE 4

| Ex. | Active ingredient | Concentration of active ingredient in the spray liquor in ppm | Efficacy in % of the untreated control |
|---|---|---|---|
| 15C | Control (untreated) | (97% infection) | 0 |
| 16C | Ia.1 | 1 | 8 |
|  |  | 0.25 | 0 |
| 17C | Ia.2 | 1 | 0 |
|  |  | 0.25 | 0 |
| 18C | II.1 | 1 | 59 |
|  |  | 0.25 | 0 |
| 19C | II.2 | 0.25 | 18 |

TABLE 5

| Ex. | Mixture according to the invention | Observed efficacy | Calculated efficacy* |
|---|---|---|---|
| 20 | 1 ppm Ia.1 + 1 ppm II.1 | 85 | 62 |
| 21 | 0.25 ppm Ia.1 + 0.25 ppm II.1 | 49 | 0 |
| 22 | 1 ppm Ia.1 + 0.25 ppm II.1 | 79 | 8 |
| 23 | 0.25 ppm Ia.1 + 1 ppm II.2 | 79 | 59 |
| 24 | 0.25 ppm Ia.1 + 0.25 ppm II.2 | 38 | 18 |
| 25 | 1 ppm Ia.1 + 0.25 ppm II.1 | 69 | 24 |
| 26 | 1 ppm Ia.2 + 1 ppm II.1 | 79 | 59 |
| 27 | 0.25 ppm Ia.2 + 0.25 ppm II.1 | 28 | 0 |
| 28 | 1 ppm Ia.2 + 0.25 ppm II.1 | 28 | 0 |
| 29 | 0.25 ppm Ia.2 + 1 ppm II.1 | 79 | 59 |
| 30 | 0.25 ppm Ia.2 + 0.25 ppm II.2 | 48 | 18 |
| 31 | 1 ppm Ia.2 + 0.25 ppm II.2 | 38 | 18 |

*)calculated using Colby's formula

The test results show that the observed efficacy in all mixing ratios is higher than the efficacy which had been calculated beforehand using Colby's formula.

We claim:

1. A fungicidal composition comprising synergistically effective amounts of a) a carbamate of formula I,

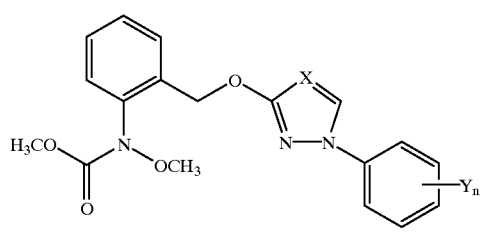

wherein X is CH, n is 0, 1 or 2 and Y is halogen, $C_1$–$C_4$-alkyl or $C_1$–$C_4$-haloalkyl, wherein the radicals Y are identical or different when n is 2, or a salt or adduct thereof, and b) an oxime ether carboxamide of formula II

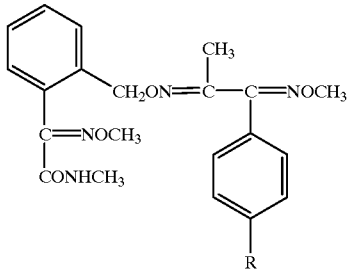

wherein R represents hydrogen or halogen.

2. The composition defined in claim 1, comprising the carbamate of formula I or a salt or adduct thereof and the carboxamide of formula II in a weight ratio of from 10:1 to 0.1:1.

3. The composition defined in claim 1 which is conditioned in two parts, one part comprising the carbamate of formula I in a solid or liquid carrier, and the other part comprising the carboxamide of formula II in a solid or liquid carrier.

4. The composition defined in claim 1 wherein Y is selected from the group consisting of fluorine, chlorine, bromine, methyl, ethyl, 2-propyl and trifluoromethyl.

5. The composition defined in claim 1 wherein R is selected from the group consisting of hydrogen, fluorine and chlorine.

6. The composition defined in claim 1 comprising the carbamate of formula I or a salt or adduct thereof and the carboxamide of formula II in a weight ratio of from 5:1 to 0.2:1.

7. A method of controlling harmful fungi, which comprises treating the harmful fungi, their habitat, or plants, seeds, soils, areas, materials or spaces to be kept free from said fungi with synergistically effective amount of the carbamate of formula I or a salt of adduct thereof as set forth in claim 1 and the carboxamide of formula II as set forth in claim 1.

8. The method of claim 7, wherein the carbamate of formula I or a salt or adduct thereof and the carboxamide of formula II are applied simultaneously, that is either together or separately, or in succession.

9. The method of claim 7, wherein the carbamate of formula I or a salt or adduct thereof is applied in an amount of from 0.01 to 1 kg/ha.

10. The method of claim 7, wherein the carboxamide of formula II is applied in an amount of from 0.01 to 1 kg/ha.

11. The method of claim 7, wherein Y is selected from the group consisting of fluorine, chlorine, bromine, methyl, ethyl, 2-propyl and trifluoromethyl.

12. The method of claim 7, wherein R is selected from the group consisting of hydrogen, fluorine and chlorine.

13. The method of claim 7, wherein the carbamate of formula I or a salt or adduct thereof is applied in an amount of from 0.05 to 0.5 kg/ha.

14. The method of claim 7, wherein the carboxamide of formula II is applied in an amount of from 0.02 to 0.5 kg/ha.

* * * * *